United States Patent
Whittaker

(10) Patent No.: US 9,004,377 B1
(45) Date of Patent: Apr. 14, 2015

(54) SCENT PRODUCING VASE ASSEMBLY

(71) Applicant: Earl C. Whittaker, Gainestown, AL (US)

(72) Inventor: Earl C. Whittaker, Gainestown, AL (US)

(*) Notice: Subject to any disclaimer, the term of this patent is extended or adjusted under 35 U.S.C. 154(b) by 0 days.

(21) Appl. No.: 13/919,354

(22) Filed: Jun. 17, 2013

(51) Int. Cl.
  *A61L 9/04* (2006.01)
  *A41G 1/00* (2006.01)

(52) U.S. Cl.
  CPC ...................... *A41G 1/006* (2013.01)

(58) Field of Classification Search
  CPC .......................................................... A61L 9/04
  USPC .......................... 422/5, 120, 124; 239/34, 311
  See application file for complete search history.

(56) References Cited

U.S. PATENT DOCUMENTS

| | | | |
|---|---|---|---|
| 5,077,102 A | 12/1991 | Chong | |
| D370,548 S | 6/1996 | Cocca et al. | |
| 5,547,721 A * | 8/1996 | Kuo | 428/34.1 |
| 5,725,152 A | 3/1998 | Akyu | |
| 5,776,561 A | 7/1998 | Lindauer | |
| 6,017,596 A | 1/2000 | Deraney | |
| 6,318,876 B1 | 11/2001 | Sigro et al. | |
| 6,581,915 B2 | 6/2003 | Bartsch et al. | |
| 7,223,361 B2 | 5/2007 | Kvietok et al. | |
| 8,052,934 B2 * | 11/2011 | Manne | 422/123 |
| 8,123,629 B2 | 2/2012 | Ladd et al. | |
| 8,137,629 B2 * | 3/2012 | Faber et al. | 422/120 |
| 2001/0051234 A1 | 12/2001 | Ryan et al. | |
| 2005/0084413 A1 * | 4/2005 | Stanley, III | 422/5 |

* cited by examiner

Primary Examiner — Sean E Conley

(57) ABSTRACT

A scent producing vase assembly holds artificial flowers and produces a scent to fully simulate the presence of real flowers in the vase. The assembly includes a vase having a bottom wall and a perimeter wall coupled to and extending upwardly from a perimeter edge of the bottom wall. An upper edge of the perimeter wall defines an opening into an interior space of the vase. A housing is coupled to and extends through the bottom wall of the vase. A scent producing element is positioned in the housing. A channel has a lower end and an upper end. The lower end is in environmental communication with the scent producing element in the housing. An opening extends through the upper end of the channel wherein the scent producing element delivers a scent to ambient air around the upper end of the channel.

16 Claims, 5 Drawing Sheets

SCENT PRODUCING VASE ASSEMBLY

BACKGROUND OF THE DISCLOSURE

Field of the Disclosure

The disclosure relates to vase devices and more particularly pertains to a new vase device for holding artificial flowers and producing a scent to fully simulate the presence of real flowers in the vase device.

SUMMARY OF THE DISCLOSURE

An embodiment of the disclosure meets the needs presented above by generally comprising a vase having a bottom wall and a perimeter wall coupled to and extending upwardly from a perimeter edge of the bottom wall. An upper edge of the perimeter wall defines an opening into an interior space of the vase. A housing is coupled to and extends through the bottom wall of the vase. A scent producing element is positioned in the housing. A channel has a lower end and an upper end. The lower end is in environmental communication with the scent producing element in the housing. An opening extends through the upper end of the channel wherein the scent producing element delivers a scent to ambient air around the upper end of the channel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
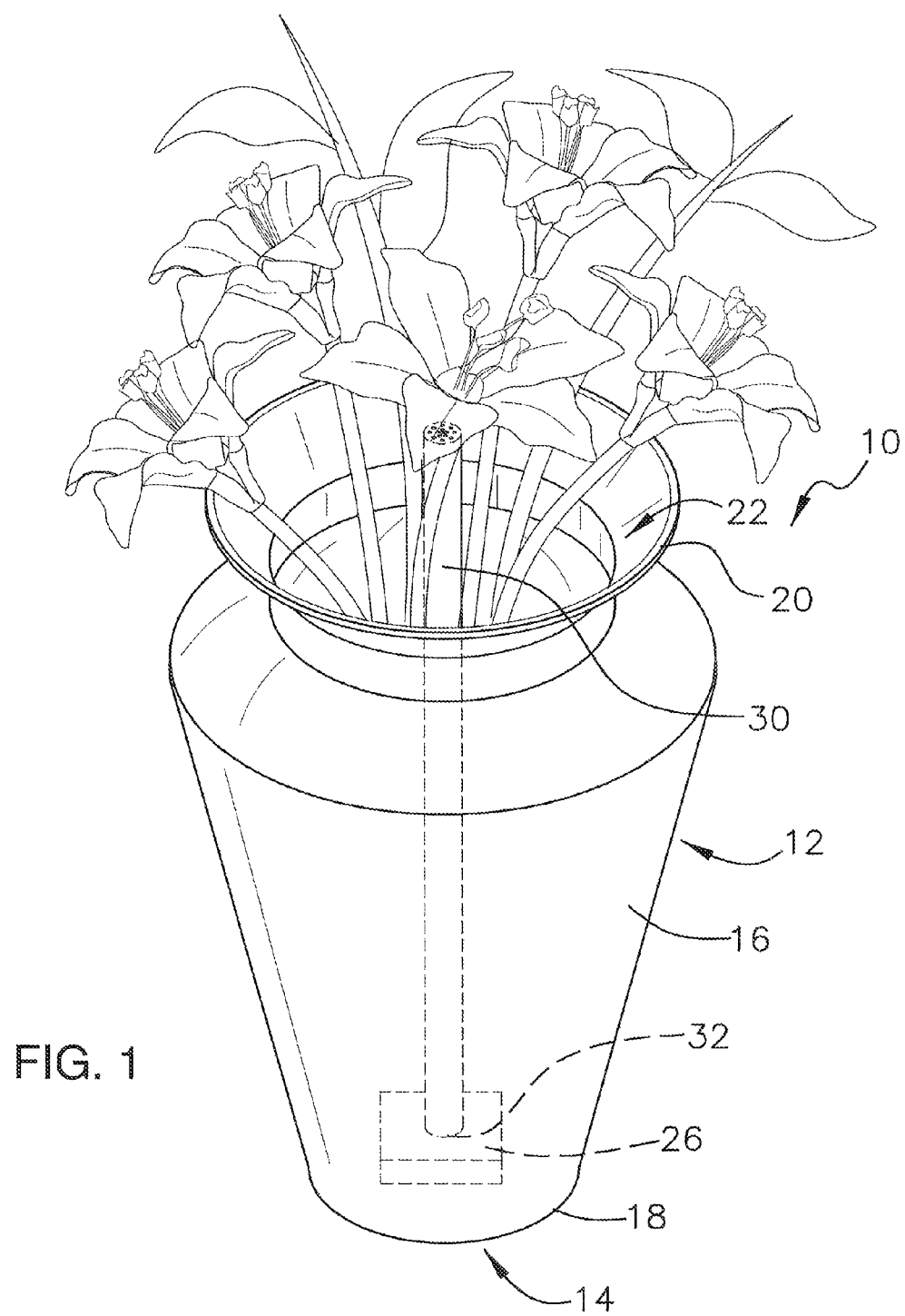
FIG. 1 is a top front perspective view of a scent producing vase assembly according to an embodiment of the disclosure.
Figure 2:
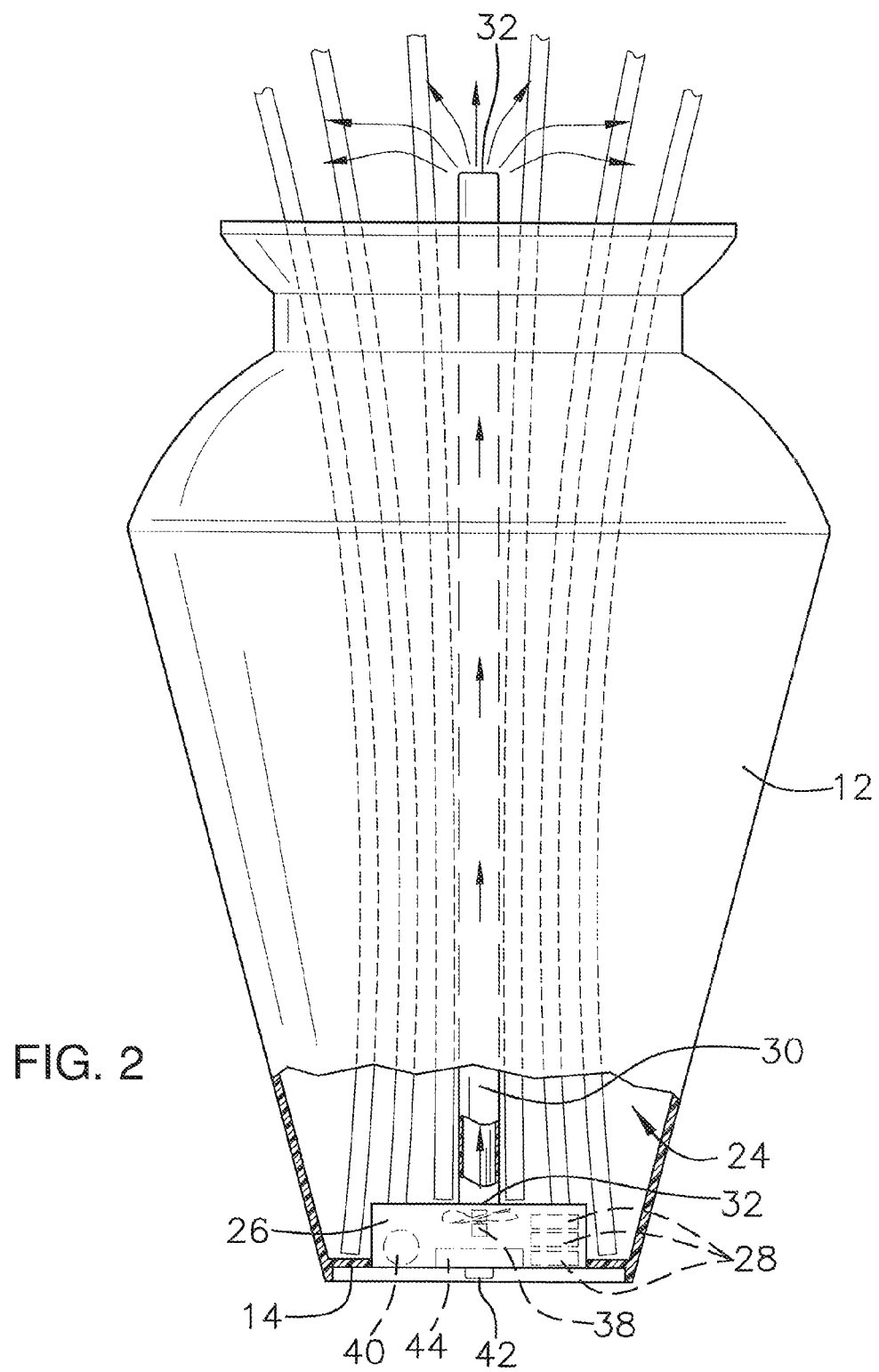
FIG. 2 is a partial cut-away front view of an embodiment of the disclosure.
Figure 3:
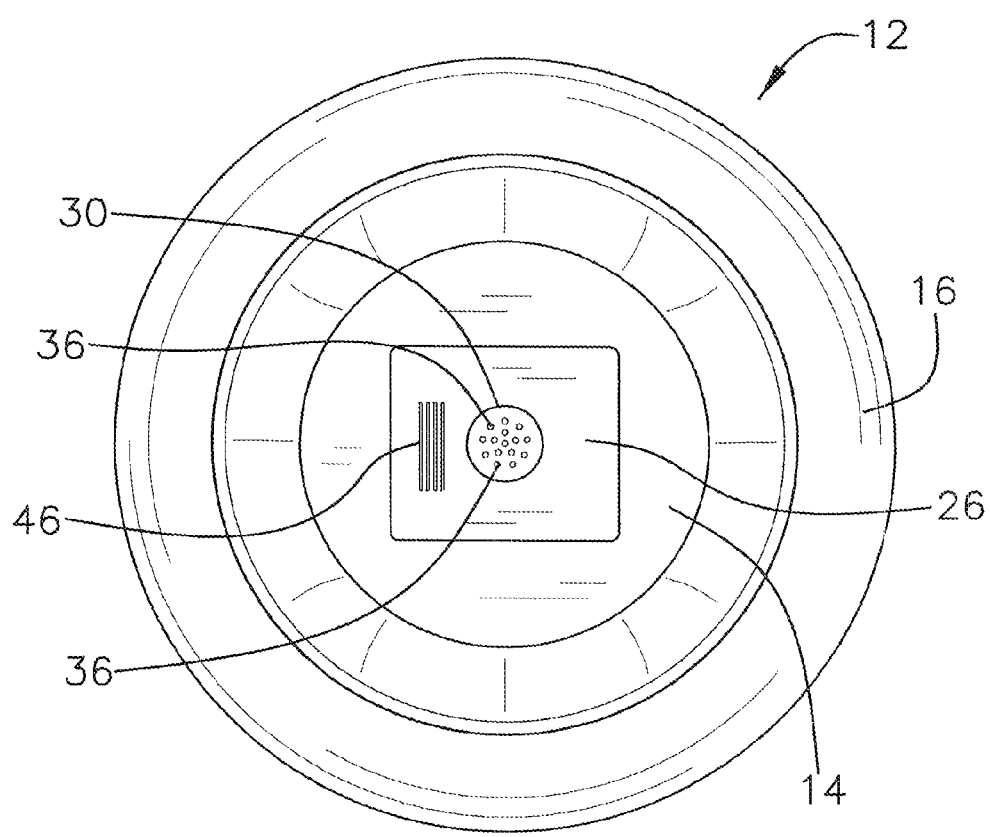
FIG. 3 is a top view of an embodiment of the disclosure.
Figure 4:
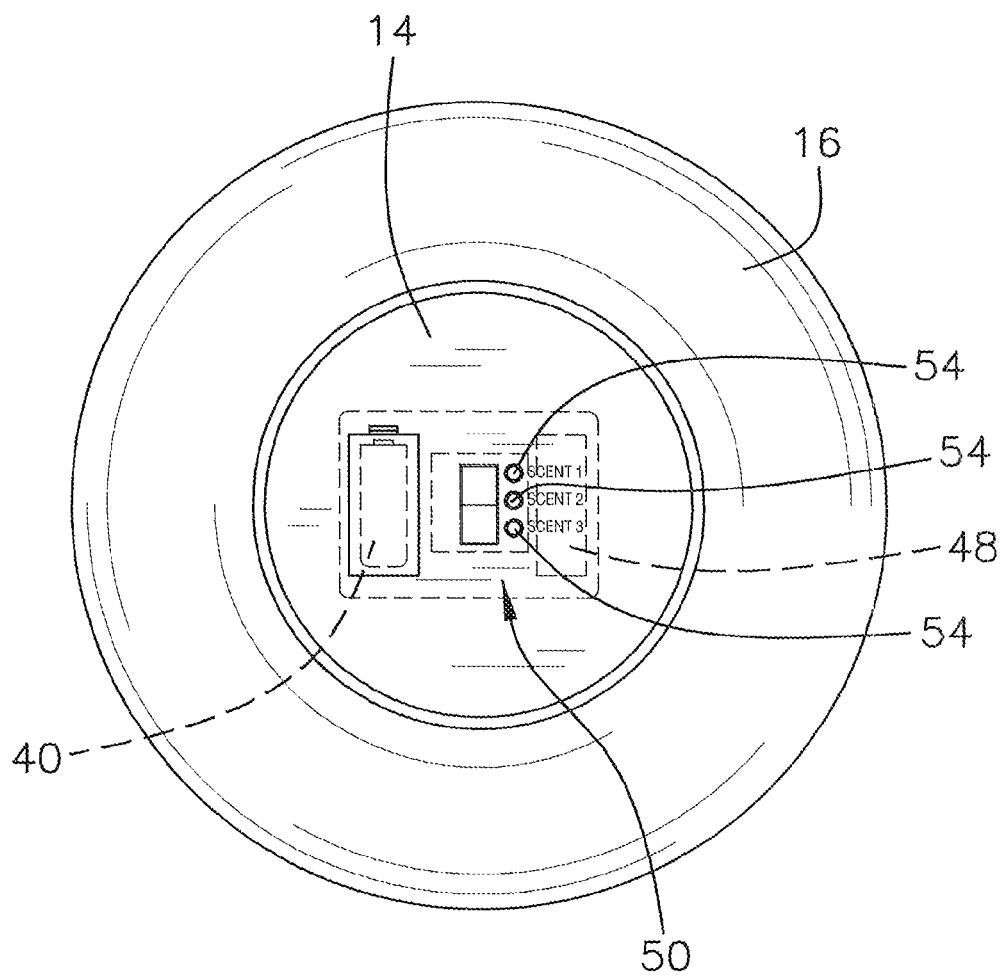
FIG. 4 is a bottom view of an embodiment of the disclosure.
Figure 5:
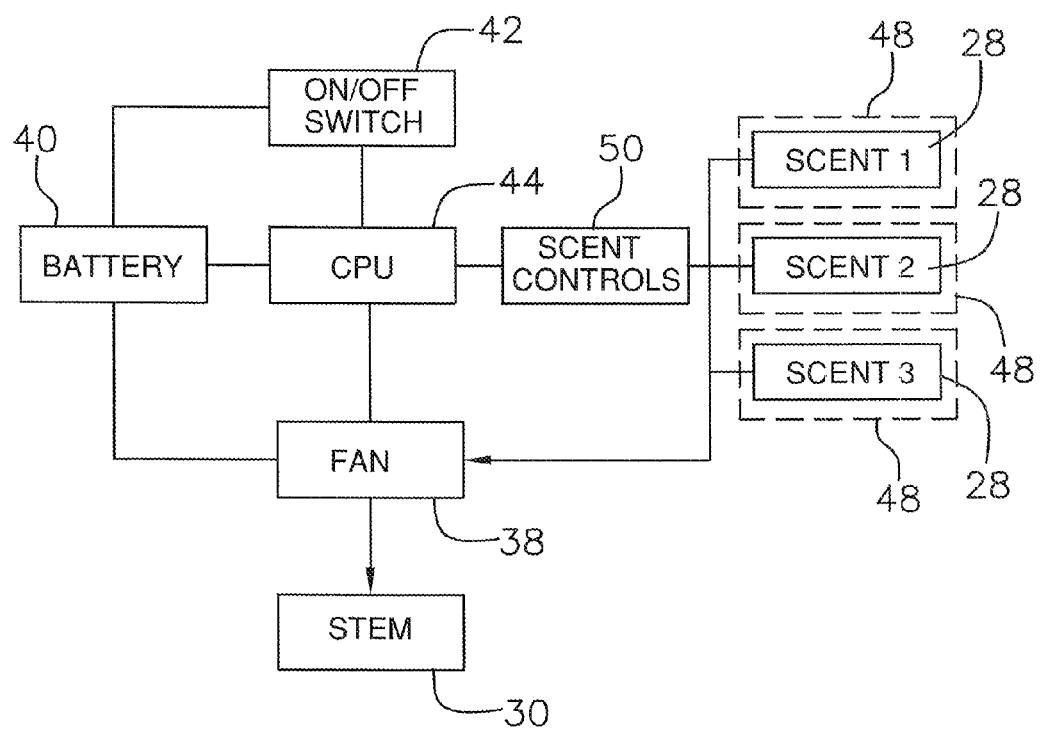
FIG. 5 is a schematic view of an embodiment of the disclosure.

With reference now to the drawings, and in particular to FIGS. 1 through 5 thereof, a new vase device embodying the principles and concepts of an embodiment of the disclosure and generally designated by the reference numeral 10 will be described.

As best illustrated in FIGS. 1 through 5, the scent producing vase assembly 10 generally comprises a vase 12 having a bottom wall 14 and a perimeter wall 16 coupled to and extending upwardly from a perimeter edge 18 of the bottom wall 14. An upper edge 20 of the perimeter wall 16 defines an opening 22 into an interior space 24 of the vase 12. A housing 26 is coupled to and extends through the bottom wall 14 of the vase 12. The housing 26 may be rectangular in shape and have a center of gravity substantially aligned with a longitudinal axis of the vase 12. A scent producing element 28 of conventional construction is positioned in the housing 26. A channel 30 has a lower end 32 and an upper end 34. The lower end 32 of the channel 30 is in environmental communication with the scent producing element 28 in the housing 26. An opening 36 is positioned in the upper end 34 of the channel 30 wherein the scent producing element 28 is configured to deliver a scent to ambient air around the upper end 34 of the channel 30. The channel 30 may be centrally positioned in the interior space 24. The channel 30 may have a length such that the channel 30 extends out through the opening 22 and the upper end 34 of the channel 30 is positioned in slightly spaced relationship above the upper edge 30 of the perimeter wall 16.

A fan 38 may be coupled to and positioned in the housing 26. The fan 38 may be positioned adjacent to the lower end 32 of the channel 30. The fan 38 urges air flow through the channel 30 from the scent producing element 28 to the upper end 34 of the channel 30. A battery 40 is coupled to and positioned in the housing 26. The battery 40 is electrically coupled to the fan 38. The battery 40 may be accessible for replacement through the bottom wall 14 of the vase 12. A switch 42 is electrically coupled between the battery 40 and the fan 38 wherein manipulation of the switch 42 selectively activates the fan 38. A processor 44 may be coupled to and positioned in the housing 26. The processor 44 may be operationally coupled to the fan 38. The processor 44 may be programmed to selectively activate the fan 38 according to a desired duration of time or periodic schedule.

A vent 46 may be coupled to and extend through the housing 26. The vent 46 may be a one-way vent in environmental communication with the scent producing element 28 wherein the vent 46 permits passage of air into the housing 26 and through the channel 30 when the fan 38 is activated. The housing 26 may be structured to include a plurality of scent compartments 48 positioned in the housing 26. Each scent compartment 48 may be in environmental communication with the vent 46 or a plurality of separate vents may also be used. A plurality of the scent producing elements 28 may be utilized with each scent producing element 28 being positioned in an associated one of the scent compartments 48. A scent control 50 is provided. The scent control 50 selectively opens each scent compartment 48 to the channel 30 in a conventional manner utilizing valves, doors, or other structure to selectively open or obstruct each scent compartment 48 from the channel 30. Thus, a strength of scent passing through the channel 30 is adjustable by manipulation of the scent control 50. The scent producing elements 28 may each be of the same scent or different scents. Thus, manipulation of the scent control 50 may provide for a stronger or weaker single scent, selection of a desired scent from unique scents, or a combination of the scents. The scent control 50 may comprise a plurality of buttons 54. Each button 54 is operationally coupled to an associated one of the scent compartments 48 to permit direct control of the release of scent from each scent compartment 48.

In use, scent producing elements 28 are selected and positioned in the scent compartments 48 in the housing 26. The processor 44 may be programmed to automatically activate the fan 38 according to a desired schedule. The scent control 50 may also be manipulated to selectively control the release of scent. Activation of the fan 38 draws ambient air through the housing 26, each open scent compartment 48, and the channel 30. Thus, scent is passed out of the channel 30. Artificial flowers or other decorative materials can be placed in the vase 12. The flowers may correspond to the particular scent being passed through the channel 30.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A scent producing vase assembly comprising:
    a vase having a bottom wall and a perimeter wall coupled to and extending upwardly from a perimeter edge of said bottom wall;
    an upper edge of said perimeter wall defining an opening into an interior space of said vase;
    a housing coupled to and extending through said bottom wall of said vase;
    a scent producing element positioned in said housing;
    a channel having a lower end and an upper end, said lower end being in environmental communication with said scent producing element in said housing, said channel comprising a tube including said lower and upper ends and a peripheral wall extending between said upper and lower ends wherein said peripheral wall has a tubular shape, said channel being free of any attachments except for said housing;
    an opening in said upper end of said channel wherein said scent producing element is configured to deliver a scent to ambient air around said upper end of said channel.

2. The assembly of claim 1, further comprising a fan coupled to and positioned in said housing, said fan being positioned adjacent to said lower end of said channel, said fan urging air flow through said channel from said scent producing element to said upper end of said channel.

3. The assembly of claim 2, further comprising a battery coupled to and positioned in said housing, said battery being electrically coupled to said fan.

4. The assembly of claim 3, further comprising said battery being accessible through said bottom wall of said vase.

5. The assembly of claim 2, further comprising a processor coupled to and positioned in said housing, said processor being operationally coupled to said fan.

6. The assembly of claim 3, further comprising a switch electrically coupled between said battery and said fan wherein manipulation of said switch selectively activates said fan.

7. The assembly of claim 2, further comprising a vent coupled to and extending through said housing, said vent being in environmental communication with said scent producing element wherein said vent is configured for passing air into said housing and through said channel when said fan is activated.

8. The assembly of claim 1, further comprising:
    a plurality of scent compartments positioned in said housing; and
    a plurality of said scent producing elements, each said scent producing element being positioned in an associated one of said scent compartments.

9. The assembly of claim 8, further comprising a scent control, said scent control selectively opening each said scent compartments to said channel wherein a strength of scent passing through said channel is adjustable by manipulation of said scent control.

10. The assembly of claim 9, further comprising said scent control comprising a plurality of buttons, each said button being operationally coupled to an associated one of said scent compartments.

11. A scent producing vase assembly comprising:
    a vase having a bottom wall and a perimeter wall coupled to and extending upwardly from a perimeter edge of said bottom wall;
    an upper edge of said perimeter wall defining an opening into an interior space of said vase;
    a housing coupled to and extending through said bottom wall of said vase;
    a scent producing element positioned in said housing;
    a channel having a lower end and an upper end, said lower end being in environmental communication with said scent producing element in said housing, said channel comprising a tube including said lower and upper ends and a peripheral wall extending between said upper and lower ends wherein said peripheral wall has a tubular shape, said channel being free of any attachments except for said housing;
    an opening in said upper end of said channel wherein said scent producing element is configured to deliver a scent to ambient air around said upper end of said channel;
    a fan coupled to and positioned in said housing, said fan being positioned adjacent to said lower end of said channel, said fan urging air flow through said channel from said scent producing element to said upper end of said channel;
    a battery coupled to and positioned in said housing, said battery being electrically coupled to said fan, said battery being accessible through said bottom wall of said vase;
    a processor coupled to and positioned in said housing, said processor being operationally coupled to said fan;
    a switch electrically coupled between said battery and said fan wherein manipulation of said switch selectively activates said fan;
    a vent coupled to and extending through said housing, said vent being in environmental communication with said scent producing element wherein said vent is configured for passing air into said housing and through said channel when said fan is activated;
    a plurality of scent compartments positioned in said housing;
    a plurality of said scent producing elements, each said scent producing element being positioned in an associated one of said scent compartments; and
    a scent control, said scent control selectively opening each said scent compartments to said channel wherein a strength of scent passing through said channel is adjustable by manipulation of said scent control, said scent control comprising a plurality of buttons, each said button being operationally coupled to an associated one of said scent compartments.

12. The assembly of claim 11, wherein said upper end of said channel extends upwardly through said opening.

13. The assembly of claim 11, wherein said channel is linear from said upper end to said lower end.

14. The assembly of claim 11, wherein said channel is centrally located within said vase such that said channel is axially aligned with said vase.

15. The assembly of claim 12, wherein said channel is linear from said upper end to said lower end.

16. The assembly of claim 15, wherein said channel is centrally located within said vase such that said channel is axially aligned with said vase.

\* \* \* \* \*